United States Patent [19]

Kaeding et al.

[11] Patent Number: 4,593,136

[45] Date of Patent: Jun. 3, 1986

[54] ZSM-5/ZSM-12 CATALYST MIXTURE FOR CRACKING ALKYLBENZENES

[75] Inventors: Warren W. Kaeding, Lawrenceville; Carol S. Lee, Princeton, both of N.J.

[73] Assignee: Mobil Oil Corporation, New York, N.Y.

[21] Appl. No.: 784,965

[22] Filed: Oct. 7, 1985

Related U.S. Application Data

[60] Division of Ser. No. 620,590, Jun. 14, 1984, which is a continuation-in-part of Ser. No. 490,624, May 2, 1983, abandoned.

[51] Int. Cl.$^4$ ............................ C07C 2/64; C07C 4/12
[52] U.S. Cl. .................................... 585/446; 585/467; 585/486
[58] Field of Search ..................... 585/446, 467, 486

[56] References Cited

U.S. PATENT DOCUMENTS

| 4,136,128 | 1/1979 | Haag et al. | 585/475 X |
| 4,188,282 | 2/1980 | Tabak et al. | 208/134 |
| 4,251,676 | 2/1981 | Wu | 585/486 |
| 4,289,606 | 9/1981 | Gladrow et al. | 208/120 |
| 4,372,839 | 2/1983 | Oleck et al. | 252/455 Z |
| 4,463,209 | 7/1984 | Kursewicz et al. | 585/486 |

Primary Examiner—Curtis R. Davis
Attorney, Agent, or Firm—Alexander J. McKillop; Michael G. Gilman; Edward F. Kenehan, Jr

[57] ABSTRACT

There is provided a mixed catalyst of ZSM-5 and ZSM-12. Alkylbenzenes, especially heavy aromatic bottoms from cumene production, may be cracked over this mixed catalyst.

4 Claims, No Drawings

ZSM-5/ZSM-12 CATALYST MIXTURE FOR CRACKING ALKYLBENZENES

CROSS-REFERENCE TO RELATED APPLICATION

This application is a division of copending U.S. Application Ser. No. 620,590, filed June 14, 1984, which is a continuation-in-part of copending U.S. application Ser. No. 490,624, filed May 2, 1983, now abandoned. The entire disclosures of these applications are expressly incorporated herein by reference.

BACKGROUND

This invention relates to a catalyst, which is a mixture of ZSM-5 and ZSM-12, and a method for cracking alkylbenzenes over this catalyst mixture.

The Tabak et al. U.S. Pat. No. 4,188,282, the entire disclosure of which is expressly incorporated herein by reference, describes a process utilizing a zeolite catalyst for converting reformer bottoms having at least 8 carbon atoms to hydrocarbon mixtures enriched in benzene, toluene and xylene (BTX).

In the process for alkylation of benzene with propylene or propane/propylene mixtures to produce cumene, di- and poly-propylated benzene derivatives and other alkylated benzene derivatives are produced as side reaction products. These products are presently utilized as relatively low value fuel.

The production of cumene (i.e. isopropylbenzene) is discussed in the Kirk-Othmer Encyclopedia of Chemical Technology, Third Edition, Volume 7, pp. 286–290, John Wiley and Sons (1979), the entire disclosure of which is expressly incorporated herein by reference.

SUMMARY

According to one aspect of the invention, there is provided a catalyst comprising a mixture of zeolites, said mixture comprising:
  (i) from about 10% to about 90% by weight of ZSM-5; and
  (ii) from about 10% to about 90% by weight of ZSM-12.

According to another aspect of the invention, there is provided a process for converting a first hydrocarbon mixture to a second hydrocarbon mixture, said first hydrocarbon mixture consisting essentially of aromatic hydrocarbons having 10 or more carbon atoms, said first hydrocarbon mixture comprising at least 50% by weight of diisopropylbenzene and less than 5% by weight of the sum of benzene, toluene, xylene and ethylbenzene, said second hydrocarbon mixture comprising at least 30% by weight of the sum of benzene, toluene, xylene and ethylbenzene and less than 20% by weight of diisopropylbenzene, said process comprising cracking said first hydrocarbon mixture over a catalyst comprising a mixture of zeolites, said mixture of zeolites consisting essentially of from about 10% to about 90% by weight of ZSM-5, the remainder being essentially ZSM-12.

According to another aspect of the invention, there is provided an improved method for the preparation of isopropylbenzene from benzene and a mixture of propane and propylene, wherein a heavy aromatic bottoms fraction is produced as a byproduct, said bottoms fraction consisting essentially of hydrocarbons having 10 or more carbon atoms, the improvement comprising cracking said bottoms fraction over a catalyst comprising a mixture of zeolites, said mixture comprising:
  (i) from about 10% to about 90% by weight of ZSM-5; and
  (ii) from about 10% to about 90% by weight of ZSM-12.

EMBODIMENTS

Catalysts and conditions of reaction have been found to remove the alkyl side chains by cracking to produce benzene which can be recovered and recycled. In certain instances, the aliphatic fragments from the cracking can also be converted to more valuable aromatic (BTX) compounds.

Examples of suitable cracking conditions are as follows. The weight hourly space velocity (WHSV) in terms of the weight of feed per unit weight of catalyst may be, e.g., from about 0.5 to about 10. The cracking temperature may be, e.g., from about 300° to about 600° C. The cracking pressure may be, e.g., less than or equal to about 500 psig. Cracking may take place in the absence of added hydrogen.

ZSM-5 is described in U.S. Pat. Nos. 3,702,886 and 3,941,871. The entire descriptions contained within those patents, particularly the X-ray diffraction pattern of therein disclosed for ZSM-b 5, are expressly incorporated herein by reference.

ZSM-12 is described in U.S. Pat. No. 3,832,449. That description, and in particular the X-ray diffraction pattern disclosed therein, is expressly incorporated herein by reference.

The specific zeolites ZSM-5 and ZSM-12, when prepared in the presence of organic cations, are substantially catalytically inactive, possibly because the intracrystalline free space is occupied by organic cations from the forming solution. The zeolites may be activated by heating in an inert atmosphere at 540° C. for one hour, for example, followed by base exchange with ammonium salts followed by calcination at 540° C. in air. The presence of organic cations in the forming solution may not be absolutely essential to the formation of these types of zeolites; however, the presence of these cations does appear to favor the formation of these special classes of zeolites. More generally, it is desirable to activate this type catalyst by base exchange with ammonium salts, followed by calcination in air at about 540° C. for from about 15 minutes to about 24 hours. In addition, these zeolites may be steamed by treatment with a water saturated atmosphere for one to 24 hours at 200° to 500° C.

When synthesized in the alkali metal form, the zeolite is conveniently converted to the hydrogen form, generally by intermediate formation of the ammonium form as a result of ammonium ion exchange and calcination of the ammonium form to yield the hydrogen form. The hydrogen forms of ZSM-5 and ZSM-12 may be referred to as HZSM-5 and HZSM-12, respectively. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline zeolites in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania, as well as ternary compositions such as silica-alumina-thoria, silica-alumina-zirconia, silica-alumina-magnesia and silica-magnesia-zirconia. The matrix may be in the form of a coegel. The relative proportions of zeolite component and inorganic oxide gel matrix may vary widely with the zeolite content ranging from between about 1 to about 99 percent by weight and more usually in the range of about 5 to about 80 percent by weight of the composite.

When the ZSM-5 and ZSM-12 are composited with porous matrix materials, the catalyst of the present invention may comprise a mixture of these zeolite/matrix composites. These composites may be in a free-flowing or fluidizable form.

The catalysts may optionally comprise an additional hydrogenation/dehydrogenation component. The amount of the hydrogenation/dehydrogenation component employed is not narrowly critical and can range from about 0.01 to about 30 weight percent based on the entire catalyst. A variety of hydrogenation components may be combined with either the zeolite and/or matrix in any feasible manner which affords intimate contact of the components, employing well known techniques such as base exchange, impregnation, coprecipitation, cogellation, mechanical admixture of one component with the other and the like. The hydrogenation component can include metals, oxides and sulfides of metals of the Periodic Table which fall in Group VIB including chromium, molybdenum, tungsten and the like; Group IIB including zinc and cadmium, Group VIIB including manganese and rhenium and Group VIII including cobalt, nickel, platinum, palladium, ruthenium, rhodium and the like, and combinations of metals, sulfides and oxides of metals of Groups VIB and VIII such as nickel-tungsten-sulfide, cobalt oxide-molybdenum oxide and the like.

COMPARATIVE EXAMPLE A

Table 1 provides data regarding the cracking of a simulated heavy bottoms fraction from cumene production with a steamed-HZSM-5 catalyst.

TABLE I

| CATALYST | Steamed-HZSM-5 | |
|---|---|---|
| Feed WHSV | 2.1 | |
| Temp, C.° | 450 | |
| Pressure | ATM | |
| TOS, hrs. | 8.0 | |
| Total Product | | |

TABLE I-continued

| CATALYST | Steamed-HZSM-5 | |
|---|---|---|
| Dist., wt % | | |
| $C_{1-5}$ Feed: | 0 | 23.3 |
| Benzene | 0 | 27.7 |
| TOL | 0 | 6.4 |
| Xyl/EB | 0 | 12.6 |
| $C_9$ | 0 | 0.9 |
| Cumene | 0.6 | 1.2 |
| NPB | 0 | 3.9 |
| $C_{10-11}$ | 11.2 | 4.5 |
| MDIPB | 80.7 | 17.0 |
| PDIPB | 0 | 0.8 |
| $C_{12}$ | 7.6 | 1.7 |
| Gas Dist., wt % | | |
| $CH_4$ | | 1.8 |
| $C_2°/C_2=$ | | 2.0/3.9 |
| $C_3°/C_3=$ | | 28.4/15.7 |
| $C_4°/C_4=$ | | 29.0/16.5 |
| Conversion, wt % | | |
| MDIPB | | 80 |
| PDIPB | | — |
| $C_{12}$ | | 78 |

Totals 46.7 for Benzene+TOL+Xyl/EB.

In Table 1 and the Tables which follow, the following abbreviations are noted: Feed WHSV stands for the weight hourly space velocity of the feed; ATM stands for atmospheric; TOS stands for time on stream; $C_{1-5}$ stands for hydrocarbons having from 1 to 5 carbon atoms; TOL stands for toluene; Xyl/EB stands for xylene plus ethylbenzene; $C_9$ stands for hydrocarbons other than cumene and n-propylbenzene having 9 carbon atoms; NPB stands for n-propylbenzene; $C_{10-11}$ stands for hydrocarbons having 10 or 11 carbon atoms; MDIPB stands for meta-diisopropylbenzene, PDIPB stands for para-diisopropylbenzene; and $C_{12}$ stands for hydrocarbons other than MDIPB and PDIPB having 12 carbon atoms. It is noted that the $C_{12}$ components of the feed stream of the present Comparative Examples and Example was essentially composed entirely of phenylhexane.

COMPARATIVE EXAMPLE B

Table II provides data regarding the cracking of a simulated heavy bottoms fraction from cumene production with an HZSM-12 catalyst.

TABLE II

| CATALYST | HZSM-12 | |
|---|---|---|
| Feed WHSV | 2.2 | |
| Temp, C.° | 450 | |
| Pressure | ATM | |
| TOS, hrs. | 6.9 | |
| Total Product | | |
| Dist., wt % | | |
| $C_{1-5}$ Feed: | 0 | 37.7 |
| Benzene | 0 | 37.1 |
| TOL | 0 | 1.2 |
| Xyl/EB | 0 | 1.4 |
| $C_9$ | 0 | 4.6 |
| Cumene | 0.6 | 8.0 |
| NPB | 0 | 3.0 |
| $C_{10-11}$ | 10.5 | 3.9 |
| MDIPB | 81.5 | 1.7 |
| PDIPB | 0 | 0.7 |
| $C_{12}$ | 7.3 | 0.7 |
| Gas Dist., wt % | | |
| $CH_4$ | | 0.6 |
| $C_2°/C_2=$ | | 0.4/2.7 |
| $C_3°/C_3=$ | | 4.6/53.7 |
| $C_4°/C_4=$ | | 2.9/29.2 |
| Conversion, wt % | | |
| MDIPB | | 98 |
| PDIPB | | — |

Totals 39.7 for Benzene+TOL+Xyl/EB.

TABLE II-continued

| CATALYST | HZSM-12 |
|---|---|
| $C_{12}$ | 90 |

EXAMPLE

Table III provides data regarding the cracking of a simulated heavy bottoms fraction from cumene production with a mixture of the HZSM-12 catalyst of Comparative Example B and the steamed-HZSM-5 catalyst of Comparative Example A combined in a 2:1 ratio, respectively.

TABLE III

| CATALYST | 2/1 HZSM-12/ Steamed-HZSM-5 | |
|---|---|---|
| Feed WHSV | 2.1 | |
| Temp, C.° | 450 | |
| Pressure | ATM | |
| TOS, hrs. | 6 | |
| Total Product Dist., wt % | | |
| $C_{1-5}$ Feed: | 0 | 29.4 |
| Benzene | 0 | 35.6 |
| TOL | 0 | 6.1 |
| Xyl/EB | 0 | 12.9 } 54.6 |
| $C_9$ | 0 | 0.9 |
| Cumene | 0.6 | 1.4 |
| NPB | 0 | 4.2 |
| $C_{10-11}$ | 11.2 | 5.3 |
| MDIPB | 80.7 | 2.6 |
| PDIPB | 0 | 0.9 |
| $C_{12}$ | 7.6 | 0.8 |
| Gas Dist., wt % | | |
| $CH_4$ | | 1.5 |
| $C_2°/C_2=$ | | 1.6/7.0 |
| $C_3°/C_3=$ | | 20.9/22.9 |
| $C_4°/C_4=$ | | 21.0/21.3 |
| Conversion, wt % | | |
| MDIPB | | 97 |
| PDIPB | | — |
| $C_{12}$ | | 90 |

As will be apparent from the data set forth in Tables I-III, the reaction conditions for the respective Comparative Examples and Example were essentially equivalent. More particularly, although some minor differences are apparent, e.g., with respect to Feed WHSV, TOS and Feed compositions, these differences would not be expected to have any significant effect on the results obtained. Therefore, any differences in the respective results are substantially solely attributable to the nature of the catalyst compositions used.

Table IV summarizes the results from Tables I-III.

TABLE IV

| CATALYST | 2/1 HZSM-12/ Stm-HZSM-5 | Steamed-HZSM-5B | HZSM-12 |
|---|---|---|---|
| TOTAL PRODUCT DIST., WT % | | | |
| $C_{1-5}$ | 29.4 | 23.3 | 37.7 |
| Benzene | 35.6 ⎫ | 27.7 ⎫ | 37.1 ⎫ |
| Toluene | 6.1 ⎬ 54.6 | 6.4 ⎬ 46.7 | 1.2 ⎬ 39.7 |
| Xyl/EB | 12.9 ⎭ | 12.6 ⎭ | 1.4 ⎭ |
| $C_9$ | 0.9 | 0.9 | 4.6 |
| Cumene | 1.4 | 1.2 | 8.0 |
| NPB | 4.2 | 3.9 | 3.0 |
| $C_{10-11}$ | 5.3 | 4.5 | 3.9 |
| MDIPB | 2.6 | 17.0 | 1.7 |
| PDIPB | 0.9 | 0.8 | 0.7 |
| $C_{12}$ | 0.8 | 1.7 | 0.7 |
| CONVERSION, WT % | | | |
| MDIPB | 97 | 80 | 98 |
| PDIPB | — | — | — |
| $C_{12}$ | 90 | 78 | 90 |

The mixture of ZSM-5 and ZSM-12 unexpectedly gave a better result for production of BTX than either alone. In retrospect, under the conditions of reaction used, it appears that the ZSM-12 functions to efficiently crack the higher alkyl aromatics to give unsubstituted and methyl benzenes. ZSM-5 in close proximity takes the $C_3+$ olefin fragments and rapidly converts them to aromatics, primarily BTX. The net effect is a surprising combination of catalytic effects at the conditions of reaction which maximize aromatics production without undesired side reactions, i.e., methane and paraffin formations.

What is claimed is:

1. In a method for the preparation of isopropylbenzene from benzene and a mixture of propane and propylene, wherein a heavy aromatic bottoms fraction is produced as a byproduct, said bottoms fraction consisting essentially of hydrocarbons having 10 or more carbon atoms, the improvement comprising cracking said bottoms fraction over a catalyst comprising a mixture of zeolites, said mixture comprising:
   (i) from about 10% to about 90% by weight of ZSM-5; and
   (ii) from about 10% to about 90% by weight of ZSM-12.

2. A method according to claim 1, wherein said bottoms fraction comprises at least 50% by weight of diisopropylbenzene.

3. A method according to claim 2, wherein said bottoms fraction comprises less than 5% by weight of the sum of the weights of benzene, toluene, xylene and ethylbenzene and the cracked bottoms fraction comprises at least 30% by weight of the sum of the weights of benzene, toluene, xylene and ethylbenzene.

4. A method according to claim 3, wherein the cracking conditions comprise a WHSV of from about 0.5 to about 10, a cracking temperature of from about 300° to about 600° C. and a cracking pressure of less than or equal to about 500 psig.

* * * * *